United States Patent
Morrow et al.

(10) Patent No.: US 9,551,669 B2
(45) Date of Patent: Jan. 24, 2017

(54) METHOD AND SYSTEM FOR CHARACTERIZING LIGHT EMITTING DEVICES

(71) Applicant: Sof-Tek Integrators, Inc., Redding, CA (US)

(72) Inventors: Daniel C. Morrow, Redding, CA (US); Jonathan Dummer, Redding, CA (US); Stanley Curtis Dodds, Redding, CA (US)

(73) Assignee: Sof-Tek Integrators, Inc., Redding, CA (US)

(*) Notice: Subject to any disclaimer, the term of this patent is extended or adjusted under 35 U.S.C. 154(b) by 142 days.

(21) Appl. No.: 14/204,113

(22) Filed: Mar. 11, 2014

(65) Prior Publication Data
US 2014/0268152 A1    Sep. 18, 2014

Related U.S. Application Data

(60) Provisional application No. 61/780,294, filed on Mar. 13, 2013.

(51) Int. Cl.
| | | |
|---|---|---|
| G01J 3/50 | (2006.01) | |
| G01N 21/66 | (2006.01) | |
| G01N 21/21 | (2006.01) | |
| G01N 21/84 | (2006.01) | |
| G01N 21/95 | (2006.01) | |
| G01J 1/42 | (2006.01) | |
| G01R 31/26 | (2014.01) | |

(52) U.S. Cl.
CPC ............ *G01N 21/66* (2013.01); *G01N 21/21* (2013.01); *G01N 21/8422* (2013.01); *G01N 21/9501* (2013.01); *G01J 3/501* (2013.01); *G01J 3/505* (2013.01); *G01J 2001/4252* (2013.01); *G01R 31/2635* (2013.01)

(58) Field of Classification Search
CPC G01J 3/501; G01J 2001/4252; G01R 31/2635
See application file for complete search history.

(56) References Cited

U.S. PATENT DOCUMENTS

| | | | |
|---|---|---|---|
| 5,729,343 A | 3/1998 | Aiyer | |
| 5,804,839 A * | 9/1998 | Hanaoka | H01L 29/452 257/103 |
| 6,303,397 B1 | 10/2001 | Chen et al. | |
| 8,593,148 B2 | 11/2013 | Morrow et al. | |
| 2009/0236506 A1* | 9/2009 | Dudgeon | G01J 1/42 250/228 |
| 2012/0038363 A1 | 2/2012 | Morrow et al. | |
| 2013/0119275 A1 | 5/2013 | Solarz | |

* cited by examiner

*Primary Examiner* — Tarifur Chowdhury
*Assistant Examiner* — Shawn Decenzo
(74) *Attorney, Agent, or Firm* — Hamre, Schumann, Mueller & Larson, P.C.

(57) ABSTRACT

Embodiments as disclosed herein provide a method and system that characterizes physical properties, such as thickness, uniformity, polarization, and/or sizes and locations of defect (e.g. defect density distribution) of crystalline structures grown on or thin films deposited on a substrate of a solid state light emitting device. The embodiments disclosed herein generally include exciting the light emitting device with an energy source and analyze optical energy emitted by the crystalline structures grown on or the thin films deposited on the substrate.

34 Claims, 12 Drawing Sheets

METHOD AND SYSTEM FOR CHARACTERIZING LIGHT EMITTING DEVICES

CROSS-REFERENCE TO RELATED APPLICATION(S)

This patent application claims priority to the provisional patent application entitled "METHOD AND SYSTEM FOR MEASURING THE THICKNESS AND UNIFORMITY OF LIGHT EMITTING CRYSTALLINE STRUCTURES", U.S. patent application Ser. No. 61/780,294, filed Mar. 13, 2013, which are incorporated herein by reference in its entirety.

FIELD OF THE INVENTION

Embodiments disclosed herein relate generally to a method and system for characterizing properties of structures of a solid state light emitting device. Particularly, embodiments disclosed herein relate to, for example, measuring thickness, uniformity, polarization, and/or a defect density distribution of crystalline structures grown on or thin films deposited on a substrate during a manufacturing process of the solid state light emitting device by analysis of photons emitted by the crystalline structures or thin films when excited by an energy source.

BACKGROUND OF THE INVENTION

There are a number of methods for characterizing crystalline structures grown on or thin films deposited on substrates, such as for example wafers made of various materials (e.g. silicon, sapphire, SiC, GaAs, InP). Many of these methods are destructive in nature, involve cutting into or etching materials from the crystalline structures or the thin films. These invasive methods may destroy the functionality of the tested structure and increase production costs and wastes. These invasive methods generally cannot be used to test every device during a manufacturing process.

Some methods are non-destructive, but they may require specialized and expensive testing equipment. For example, some methods use electromagnetic radiation (e.g. radio, UV, X-ray) to interact with the tested structures in a way allowing the tested structures to be characterized. The characterization is performed by measuring the strength of the reflection, absorption, diffraction, or polarization of the emitted radiation. Specialized equipment to generate stimulating radiation may be required.

SUMMARY OF THE INVENTION

In the industry of making a solid state light emitting device, manufacturers are interested in determining physical properties, such as uniformity, thickness, polarization, and sizes and locations of defects of the crystalline structures grown on or thin films deposited on substrates early in the manufacturing process. The quality of the light emitting device is based on number of and type of defects, the uniformity of the films, and/or other physical properties.

There are needs for methods and systems that can characterize crystalline structures grown on or thin films deposited on substrates that are non-intrusive. Embodiments as disclosed herein provide a method and a system that can characterize physical properties, such as thickness, uniformity, polarization, and sizes and locations of defects (e.g. defect density distribution) of the crystalline structures grown on or thin films deposited on the substrate. The embodiments disclosed herein generally include exciting individual light emitting structures (e.g. the crystalline structures grown on or the thin films deposited) on the substrate and analyzing optical energy (e.g. photons) emitted by the light emitting structures to analyze the physical properties of the light emitting structures.

In some embodiments, electricity may be used as an energy source to excite a light emitting device being tested. The crystalline structures grown on or thin films deposited on the substrate may be excited to emit photons (e.g. optical energy) by the electricity. The light emitted may be measured and de-convolved to analyze, for example, physical properties of individual structures that have emitted photons. In some embodiments, the de-convolution may be performed with at least one Gaussian function. In some embodiments, each Gaussian function may be associated with an independent physical property of the individual structures that have emitted photons.

A total optical emission in form of a spectral power distribution (SPD) is a convolution of one or more sources of radiant energy (e.g. photons) emitted by a light emitting device. In some embodiments, SPDs of the light emitting structures (e.g. crystalline structures grown on or thin films deposited on the substrate) may be collected and de-convolved to analyze the SPDs.

In some embodiments, a de-convolved SPD of the emitted photons may be analyzed. The de-convolved SPD of the emitted photons are correlated to, for example, location, size, thickness, distribution of the defects (e.g. dislocation structures) of the crystalline structures grown on or thin films deposited on the substrate. In some embodiments, a numerical wavelength parameter of the de-convolved SPD may be calculated. In some embodiments, a false color map of a numerical wavelength parameter of each device on a wafer may be used to visualize non-uniformities of the optical emission. In some embodiments, de-convolution can help reveal a subset of variations underneath the false color map. In some embodiments, one or more de-convolved SPDs may be used to construct the false color map. In some embodiments, each of the de-convolved SPDs may be associated with changes in one photon emission mechanism. By analyzing the de-convolved SPDs, multiple photon emission mechanisms may be analyzed.

BRIEF DESCRIPTION OF THE DRAWINGS

FIG. 6A illustrates a spatial distribution of dominant wavelength of the emitted photons. FIGS. 6B to 6D illustrate a first set of spatial distributions of color parameters. FIG. 6B illustrates a spatial distribution of photons intensities. FIG. 6C illustrates a spatial distribution of photon center wavelengths. FIG. 6D illustrates a spatial distribution of photon curve widths. FIGS. 6E to 6G illustrate a second set of spatial distributions of color parameters. FIG. 6E illustrates a spatial distribution of photons intensities. FIG. 6F illustrates a spatial distribution of photon center wavelengths. FIG. 6G illustrates a spatial distribution of photon curve widths.

DETAILED DESCRIPTION

A total optical emission, for example in a form of SPD, is a convolution of various photon sources such as, for example, those found in a solid state light emitting device (e.g. quantum well or QW). In one embodiment of the present invention, a signal processing method involving de-convolution of the SPD with one or more Gaussian functions may be used to characterize individual light emitting structures (e.g. crystalline structures grown on or thin films deposited on the substrate) of a substrate by analyzing the emitted photons of the individual light emitting structures. By combining the analysis results of the individual light emitting structures on the substrate in a spatial relationship, physical properties such as, for example, thickness of the layer, uniformity of the material distributed, polarization, dopant density, crystalline lattice dislocations, and/or sizes and locations of defects of the light emitting structures on the substrate may be characterized.

Typically, a solid state light emitting device, such as a high brightness light emitting diode (HBLED), includes at least one light emitting structure. The individual light emitting structures may emit photons with different properties, such as quantity (e.g. intensity) and energy (e.g. wavelength) when excited. The quantity and/or energy of these emitted photons may be correlated to physical properties of the light emitting structures and/or operating conditions. The physical properties of the light emitting structures may include, for example, thickness, uniformity, polarization, and/or sizes and locations of defects (e.g. defect density distribution). The operating conditions may include, for example, a temperature, a property (e.g. forward current) of a stimulating energy source (e.g. electricity), the duration of the stimulating energy source, and a device age. The term "device age" generally refers to time-dependent changes of performance (e.g. light emitting performance) of a device. By de-convolving the total optical emission with one or more Gaussian functions, one or more sets of color parameters reflecting the physical properties of the light emitting structures may be obtained.

Figure 1:
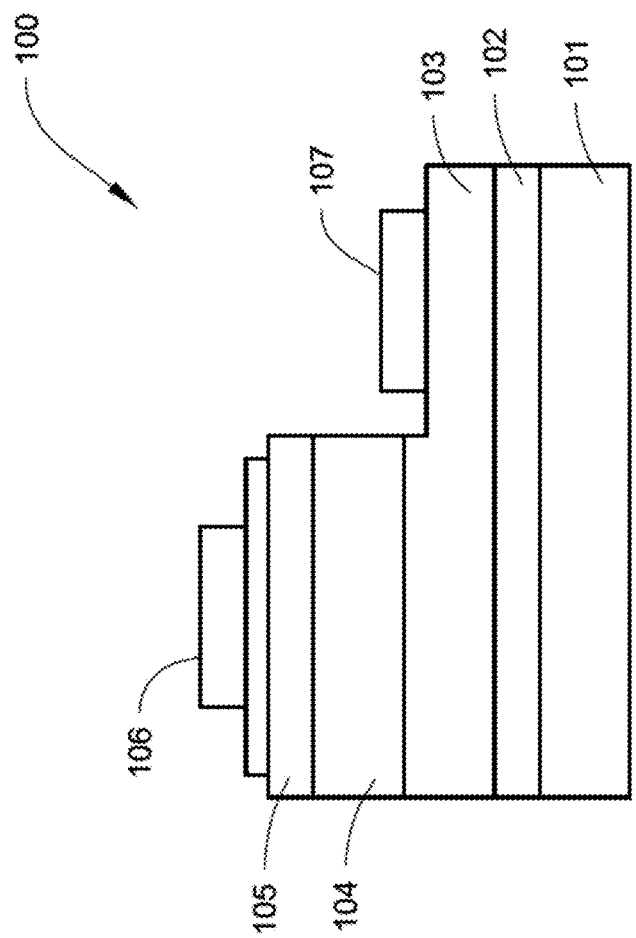
FIG. 1 illustrates an embodiment of a solid state light emitting device.

FIG. 1 shows an example of a solid state light emitting device 100, e.g. a HBLED. The solid state light emitting device 100 has more than one layer. In the illustrated embodiment, the solid state light emitting device 100 has a sapphire substrate 101. Layers sequentially deposited on top of the sapphire substrate 101 may include a gallium nitride buffer layer (GaN buffer layer) 102, a n-type gallium nitride (n-GaN) layer 103, multiple quantum wells (MQWs) 104, a p-type gallium nitride (p-GaN) layer 105. A P-contact 106 may be deposited on top of the p-GaN layer 105. A N-contact 107 may be deposited on top of the n-GaN layer 103. The MQW 104 may be excited by an energy source (e.g. electricity) to emit photons.

Figure 2:
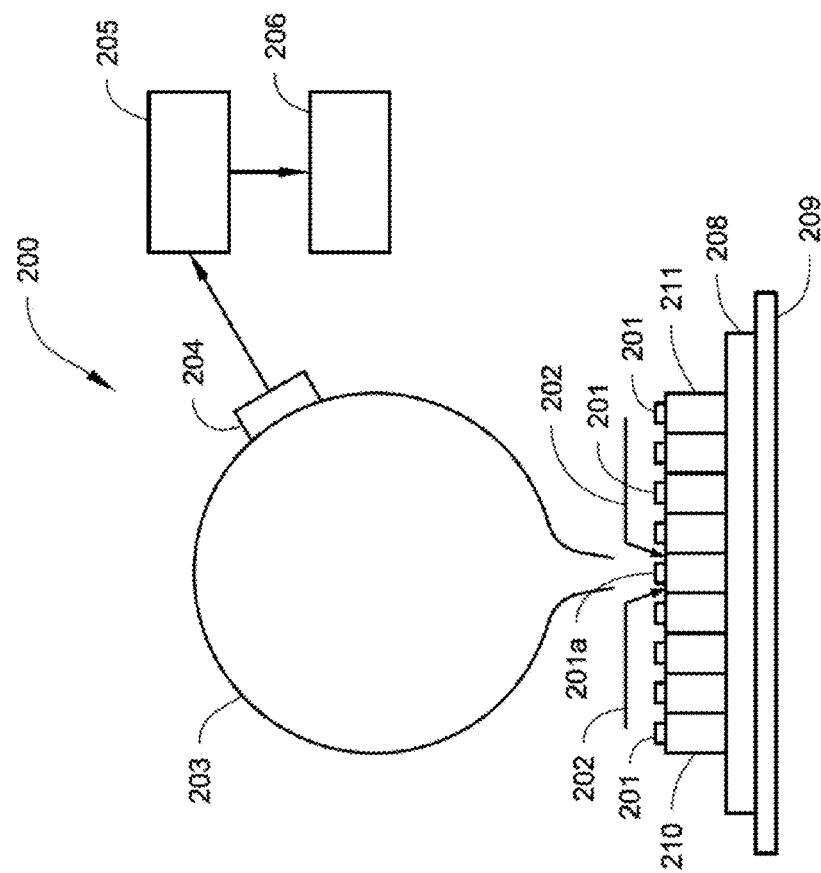
FIG. 2 illustrates an embodiment of a testing apparatus of a system for characterizing a light emitting device in accordance with the principles of the present invention.

Referring to FIG. 2, an apparatus 200 to characterize a solid state light emitting device 210 includes a probe 202, a device carrier 208, and a movable platform 209 configured to move the device carrier 208. A solid state light emitting device 210 may be positioned on the device carrier 208 and moved with the movable platform 209.

A process of characterizing individual light emitting structures (dies 201) disposed on a substrate 211 may include securing the substrate 211 on the device carrier 208. The movable platform 209 may move in two dimensions so that the individual dies 201 may be aligned with the probe 202 to test the properties of the dies 201.

While testing a specific die 201a, the probe 202 may be electrically coupled to the tested die 201a. The probe 202 is also electrically coupled to an external power source (not shown). The tested die 201a may be electrically excited so as to emit photons. An integrating sphere 203 positioned above the tested die 201a collects the emitted photons. A sensor 204 is configured to sample at least a portion of the emitted photons through the integrating sphere 203. This sampling may accurately represent a total optical emission from the tested die 201a. The sensor 204 sends the received signals to a spectrometer 205. The spectrometer 205 may be configured to convert the total optical emission into SPDs. A color analysis calculation unit 206 may be configured to analyze the SPDs, including, for example, de-convolutions, correlations, estimations, calibrations of the photons emitted by the tested die 201a.

In some embodiments, the color analysis calculation unit 206 may include a central processing unit, a storage device, a display device displaying the data stored in the storage device, an interface such that a user may interact with the calculation unit 206. In some embodiments, the color analysis calculation unit 206 may include a central processing unit, a storage device, a display device displaying the data stored in the storage device, an interface for exchanging data with the calculation unit 206.

While testing the dies 201, a temperature of the dies 201, the electrical current given to the dies 201 and device age may be controlled. U.S. Patent Publication US20110025337, issued as U.S. Pat. No. 8,593,148, on Nov. 26, 2013, discloses one method to control a temperature and/or an electrical current when testing a HBLED. The reference is incorporated herein by reference on its entirety.

Figure 3:
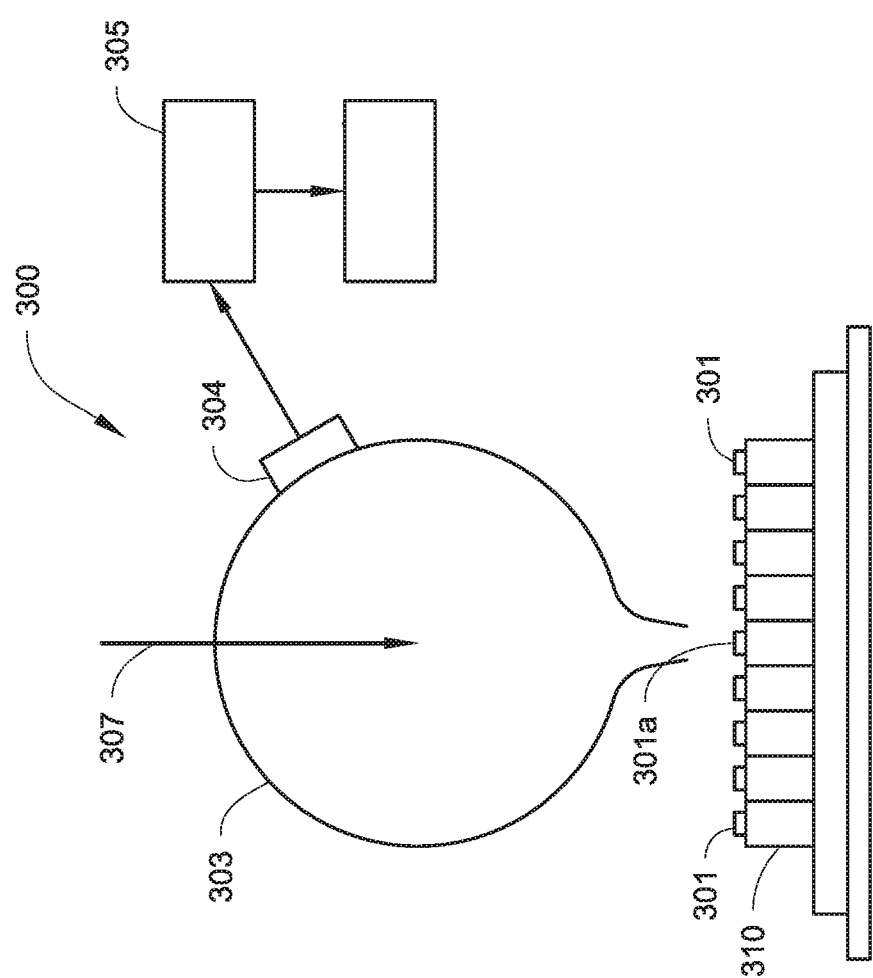
FIG. 3 illustrates another embodiment of a testing apparatus of a system for characterizing a light emitting device with excitation radio waves in accordance with the principles of the present invention.

The dies 201 as illustrated in FIG. 2 may be excited by other energy sources. For example, in another testing apparatus 300, as shown in FIG. 3, an external light source 307 may be used to excite the dies 301 of a light emitting device 310. The external light source 307 may have an excitation radio wave to excite at least some components, such as a phosphor layer of the dies 301.

The emitted light by a tested die 301a may then be sampled by the sensor 304 through the integrating sphere 303. The sensor 304 sends the received signals to the spectrometer 305. It is to be appreciated that the external light source 307 and the electrical source as mentioned in FIG. 2 may be used independently or in combination. It is also appreciated that generally an energy source that can excite the dies (e.g. the die 210, 310) may be used.

It is to be appreciated that the apparatuses as illustrated in FIGS. 2 and 3 are exemplary. Generally, an apparatus to characterize physical properties of the light emitting structure may include a probe configured to excite a light emitting structure (or region) of a light emitting device by an energy source, a device configured to collect the photons excited by the light emitting structure (or region) and a device to measure a total SPD of the photons. The apparatus may include a device configured to de-convolve the total SPD by using one or more Gaussian function to obtain a series of color parameters to describe the photons emitted by the light emitting structure (or region). The apparatus can be configured to move the light emitting device so that different light emitting structures (or regions) may be characterized. A spatial distribution of, for example, the color parameters may be obtain, which can be used to reflect properties of the light emitting device in a wafer substrate level In one embodiment, the measured total optical emission, in the form of a total SPD, is subjected to an analysis that is configured to de-convolve the total SPD into one or more Gaussian functions or other mathematical functions (e.g. Boltzmann distribution, Airy function). Each Gaussian function may include one or more color parameters, such as various intensities, curve widths, and/or center wavelengths. The characteristics of the individual Gaussian function may then be used to measure or characterize various physical properties of the die (e.g. the die 201 or 301). The spatial distribution of the characteristics of the Gaussian functions (e.g. color parameters) of the dies on the light emitting device may then be used to measure or characterize various physical properties of the light emitting device (e.g. solid state light emitting device 210 or 310), which may include thickness, uniformity, polarization, and/or a defect density distribution of crystalline structures grown or thin films deposited on a substrate.

For example, in one embodiment, a total optical emission of a HBLED is a convolution of all the individual emission mechanisms, e.g., MQWs stimulated by electricity, an emission mechanism(s) within the MQW region (e.g. heavy hole, light hole, optical phonons, quantum tunneling), phosphors stimulated by light, etc. The total optical emission is represented by a total SPD. Each of the emission mechanisms is characterized by using one or more (e.g. two or more) Gaussian functions. The characterization process includes de-convoluting the total SPD with at least one Gaussian function. Each Gaussian function may be defined by one or more color parameters (or the combination thereof) such as, for example, a height of the curve peak (e.g. intensity), the center of the peak (e.g. a center wavelength), and the width of the curve (e.g. the standard deviation). A method of using one or more color parameters to model the SPD is described in US Patent Publication US20120038363 A1, which is incorporated herein by reference on its entirety.

In some embodiments, the SPD characterization process may include applying estimation processes to optimize the color parameters of the Gaussian functions such that the summation of the Gaussian functions produces minimum errors defined by that specific estimation process. Different estimation processes may be applied, such as a least square estimation. It should be understood that other estimation process may be used.

The color parameters are associated with the physical properties of, for example, light emitting structures (e.g. crystalline structures or thin films) of the light emitting device (e.g. HBLED). These physical properties of the light emitting device may include, for example, thickness of the layer, uniformity of the material distributed, dopant density, crystalline lattice dislocations, a defect density distribution, etc. By characterizing individual light emitting structures, the physical properties of the light emitting device are characterized.

In one embodiment, for example, the tested solid state light emitting device may be a monochromatic HBLED. A total SPD of the monochromatic HBLED may be characterized with three Gaussian functions, which results in less than 0.1% of error. In this embodiment, nine color parameters may be produced (three color parameters for each Gaussian function). The estimation process optimizes the color parameters such that the summation of the three Gaussian functions produces an optimal curve fitting according to a specific estimation process.

In another embodiment, the tested solid state light emitting device may be a blue phosphor HBLED, in which a portion of the blue light emitted by the active region is absorbed by a phosphor layer which in turn emits light with, for example, longer wavelengths. This blue phosphor HBLED is sometimes referred as a white light LED. The total SPD of such blue phosphor HBLED in this embodiment is produced with six Gaussian functions, and eighteen color parameters (three color parameters for each Gaussian function) are produced. In this embodiment, the color parameters may be used to analyze a result of a phosphor interaction in the blue phosphor HBLED. That is, given a SPD of a blue phosphor HBLED and energy transfer functions of the phosphors, the color parameters are used to analyze and predict the interactions between the blue light and the phosphors. The energy contributions of the blue light from an active region and the light with a longer wavelength emitted by the phosphor layer may be separated in a de-convolution process. The contribution of different mechanisms, e.g. the active region and the phosphor, are separately characterized with different sets of color parameters. It is to be understood that the method described herein may be used to analyze and predict other phosphor interactions or solid state light emitting device including more than one LED (e.g. RGB white light LEDs), and that it is not limited to blue light/phosphor interaction.

Referring back to FIG. 2, in one embodiment, characterizing the solid state light emitting device 200 is performed by the color analysis calculation unit 206. The color analysis calculation unit 206 estimates the optimized color parameters and performs the de-convolutions. In another embodiment, the color analysis calculation unit 206 displays the color parameters in one or more figures, such as a two dimensional false color map. Such a data presentation helps visualize the physical properties of the light emitting structures distributed on a substrate of a light emitting device. In another embodiment, the color analysis unit 206 may include a central processing unit, a memory storage unit, and a data display apparatus. In another embodiment, the color analysis unit 206 may include a central processing unit, a memory storage unit, and an interface for exchanging data with the calculation unit 206.

The SPD of a solid state light emitting structure may change with variations of device conditions such as a device temperature, a stimulating electric current intensity, the time duration of the stimulating electric current, and a device age of the light emitting device itself. In some embodiments, predictions of the correlations between the SPD and the variations of device conditions may be achieved.

In one embodiment, the SPDs may be characterized under different device temperatures and a series of sets of corresponding color parameters may be obtained. An association between the SPDs and the device temperatures may be established. The SPDs may be de-convolved to color parameters, which may be used to describe how photon emission changes as a function of the device temperatures.

In another embodiment, the SPDs may be characterized under different stimulating current intensities, and a series of corresponding color parameters may be obtained, so that an association between the photons emission changes as a function of the current intensities may be established. In another embodiment, the SPDs may be characterized under different durations of stimulating current and a series of corresponding color parameters may be obtained, so that an association between the photon emission changes as a function of the duration of the stimulating current may be established. In another embodiment, the SPDs may be characterized under different ages of the light emitting structure, and a series of corresponding color parameters may be obtained, so that an association between the photon emission changes and the ages of the light emitting device may be obtained.

These associations may be established, for example, in a laboratory setting. Predictions of the correlations between the SPDs and the device conditions may be obtained by using these associations when an actual light emitting device is characterized.

In some embodiments, spatial correlation of color parameters of different light emitting structures or regions of a light emitting device may be used to characterize physical properties of the light emitting device at a wafer substrate level.

In one embodiment, the color parameters may be used to measure a crystalline structure uniformity distributed at a wafer substrate level. A solid state light emitting device may include one or more dies. Each die may include at least one light emitting structure, e.g., QW or MQW. A set of color parameters may be obtained by characterizing the emitted SPDs of the light emitting structure on each die by, for example, Gaussian functions. The analysis may be performed on multiple structures or regions on the light emitting device, and a set of color parameters can be obtained for each structures or regions. In some embodiments, this process may be performed for every die on the light emitting device. By spatially correlating the color parameters obtained from each of the dies, the structure uniformity distribution at a wafer substrate level may be obtained and visualized.

Figure 4:
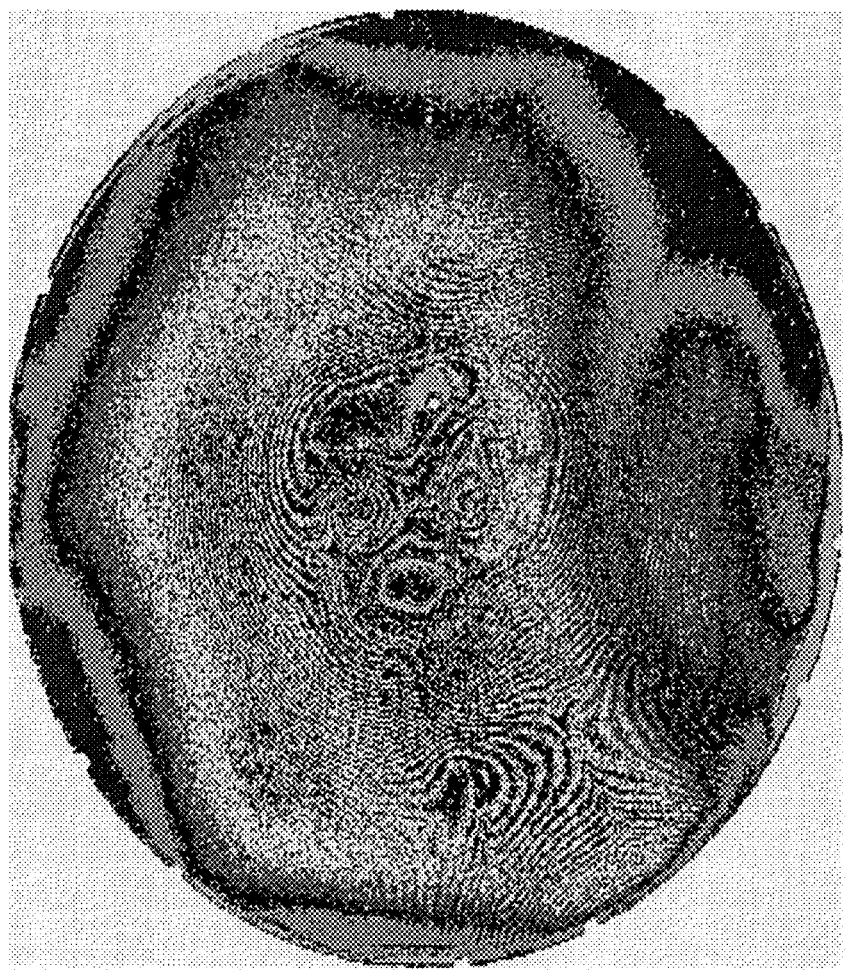
FIG. 4 illustrates an exemplary distribution of a thickness of a phosphor light-emitting layer in a blue phosphor high brightness light emitting diode deposited as dies on a wafer substrate.

For example, a set of color parameters may be used to characterize a phosphor layer thickness for a die. FIG. 4 shows a distribution of a thickness of phosphor layers of blue phosphor HBLEDs deposited on a substrate. The darker portion correlates to a relatively thick phosphor layer, and the lighter portion correlates to a relatively thin phosphor layer. The distribution of the darker portions and the lighter portions helps visualize the layer thickness distribution on the wafer substrate level.

FIG. 4 is to be understood as illustrative in nature and not restrictive. Similar processes may be repeated from substrate to substrate. In some embodiments, measurements of uniformity variations of substrate-to-substrate or lot-to-lot may be achieved by comparing the distributions of different substrates or lots. The embodiments as disclosed herein may provide a quality control method that is accurate, fast to perform, and cost effective.

False color maps may also be used to help visualize, for example, the uniformity of the light emitting device at a wafer substrate level.

Figure 5:
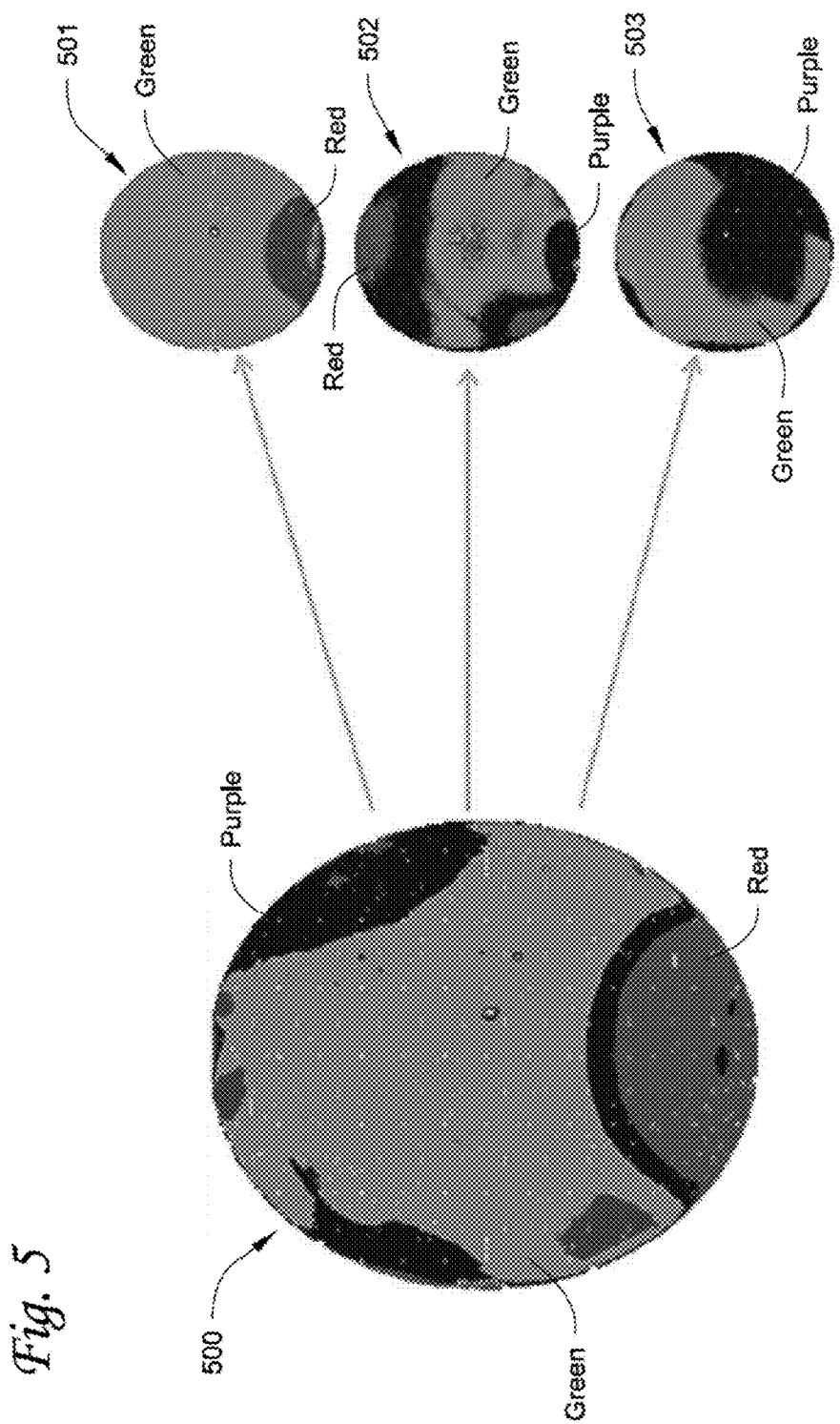
FIG. 5 illustrates an exemplary false color map at a wafer substrate level.

FIG. 5 illustrates measuring and visualizing variations and uniformities of the crystalline structures of an HBLED at a wafer substrate level with false color maps 500, 501, 502 and/or 503. Each die of a solid state light emitting device is individually tested using, for example, a testing apparatus similar to what is shown in FIG. 2 or FIG. 3. The SPDs measured from each die may be collected and analyzed. Numerical wavelength parameters of the SPDs are plotted at a wafer substrate level based on spatial distribution of the dies by false colors to visualize the numerical wavelength parameters of the SPDs. Different colors, e.g. green, red and purple, may be used to represent the distribution of the numerical wavelength parameters. For example, in some embodiments, peak wavelength values from 445-449 nm may be represented by the green color, peak wavelength values from 450-454 nm may be represented by the purple color, and peak wavelength values from 455-459 nm may be represented by the red color).

The false color map 500, which represents an overall dominant wavelength distribution, may be further de-convolved to analyze a subset of variations. In the illustrated embodiments, the subset of variations may be visualized by a subset of false color maps 501, 502 and/or 503. It is to be appreciated that the false color map 500 may be de-convolved to a subset that includes more false color maps. The false color map 500 is an aggregation or convolution of changes in several emission mechanisms. By de-convoluting the false color map 500 to the subset of false color maps 501, 502 and/or 503, different emission mechanisms may be characterized individually. Each of the subsets (e.g. the false color maps 501, 502, and/or 503) of false color map 500 may include different color parameters, e.g. different wavelengths.

Similar analyses may also be done for multiple substrates from different production lots, so that lot-to-lot variations may be analyzed.

It is to be appreciated that the embodiments as disclosed herein are not destructive, do not rely on radiation to excite crystalline structures. Because the tested structure may be characterized under its normal operation conditions, the embodiments may be applied directly on a production line during a manufacturing process. The embodiments as disclosed herein may also allow testing every device on the production line during the manufacturing process. These can help significantly reduce the cost of manufacturing and increase the quality of the device.

It is to be appreciated that the embodiments as disclosed herein may also be applied to other devices, such as a laser, or other devices including photodiodes or transistors. Generally, the embodiments as disclosed herein may be applied to a device that includes solid state structure (e.g. LED, organic light emitting diode (OLED), etc.) that can emit photons when excited by an energy source. The embodiments as disclosed herein may be applicable when the photon emitting solid state structure can be modeled with a mathematical distribution, e.g. Boltzmann or Gaussian distribution. The embodiments as disclosed herein may be applicable even when the light emission mechanisms are mixed with another photonic interaction (e.g. blue LED coated with a phosphor film).

Generally, the color parameters may be used to express the SPD in the form of a series of Gaussian distribution functions. For example, in some embodiments, the LED spectral emissions may be accurately expressed with 2 or 3 Gaussian functions and one magnitude term. Coefficients of the Gaussian functions can be mathematically manipulated (e.g. normalized and/or scaled) for manufacturing applications. The collection of the coefficients is referred as color parameters.

In some embodiments, three color parameters may be used for each Gaussian functions. When, for example, a LED emission is expressed with two Gaussian functions, a total of six color parameters and one magnitude parameter may be used.

Individual types of variations in the physical properties of deposited films (thickness, doping levels, size of dislocations, etc.) may have distinct impacts on one or more of the individual color parameters. Thus, the color parameters can be used for identifying, locating and quantizing variations in the films.

In some embodiments, when the phosphor layers are evaluated, the photon emission may require more Gaussian functions to express. For example, five or six Gaussian functions may be used to express an interaction between a blue LED and a phosphor layer, which may include a total of eleven to thirteen color parameters). Two to Three of the Gaussian functions may be used to describe the blue LED emissions, and the remaining two to three Gaussian functions can be used to describe the photon emission of the phosphor layer. The color parameters may be used to effectively split the portion of the combined blue LED and the phosphor photon emission into emissions from the phosphor layer and emissions from the blue LED. In some embodiments, the spectral of the blue LED spectral emissions may be obtained, for example, in a laboratory setting, so that the color parameters to describe the blue LED can be obtained in the laboratory. An analysis of the blue/phosphor color parameters can be performed to determine the energy conversion properties of the phosphor layer, which can be used to determine the quality and variations of the phosphor layer. The embodiments as disclosed herein can be extended to applications including more than one LED type, more than one color of the LED, and/or other types of photon emission mechanisms (e.g. phosphorescent or fluorescent).

Exemplary Embodiment

Figure 6A:
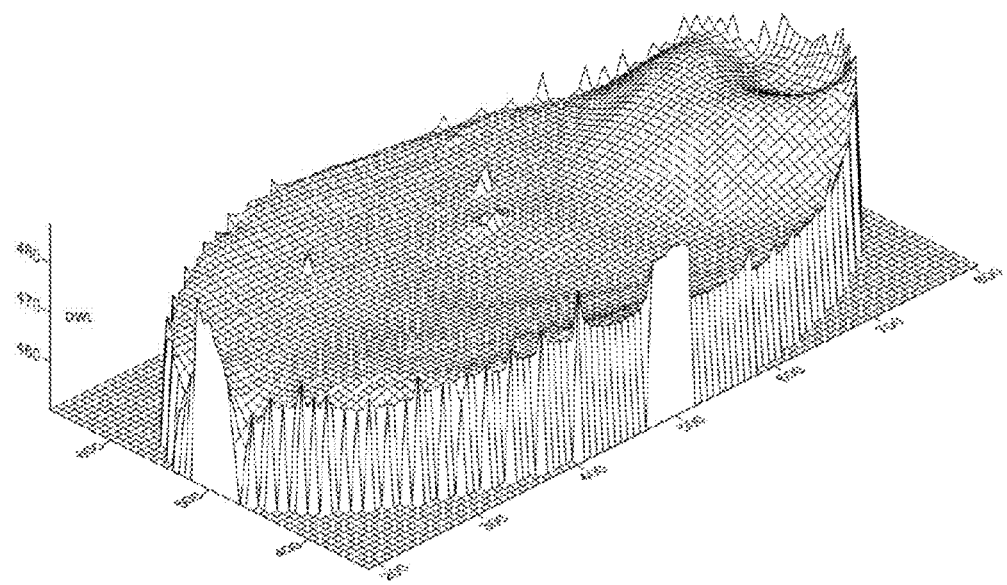
FIGS. 6A to 6G illustrate surface plots of exemplary spatial distributions of various parameters for photons emitted by a light emitting device in accordance with the principles of the present invention.
Figure 6B:
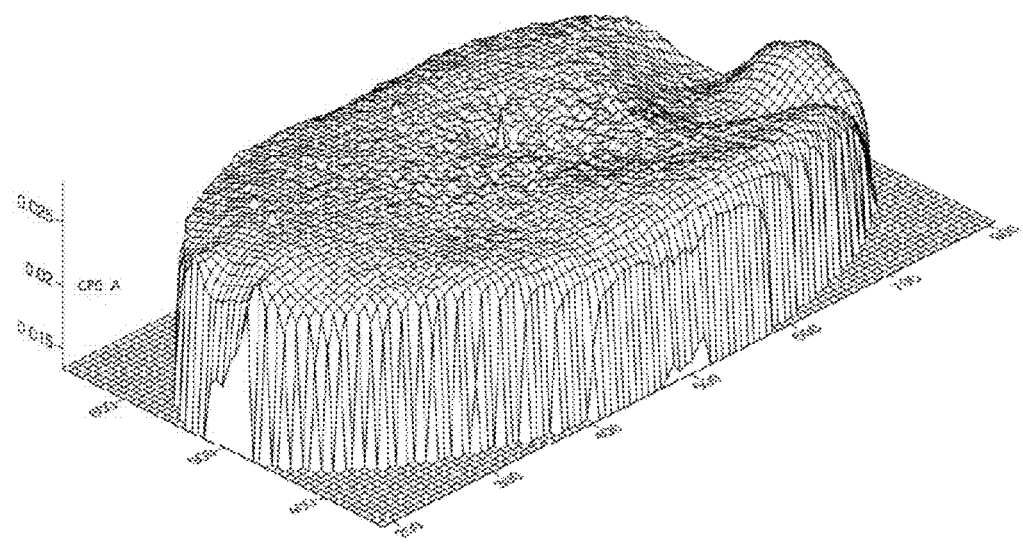
Figure 6C:
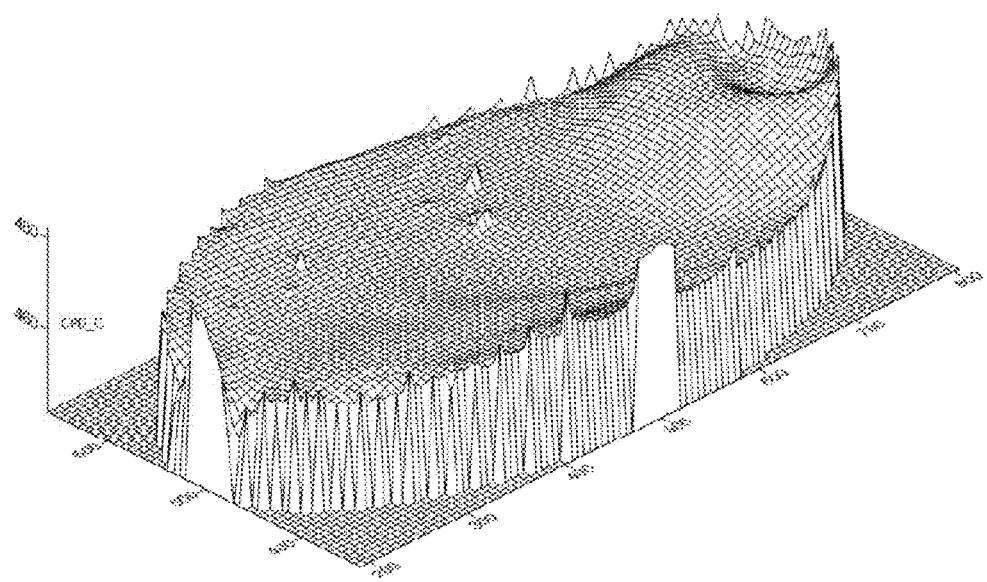
Figure 6D:
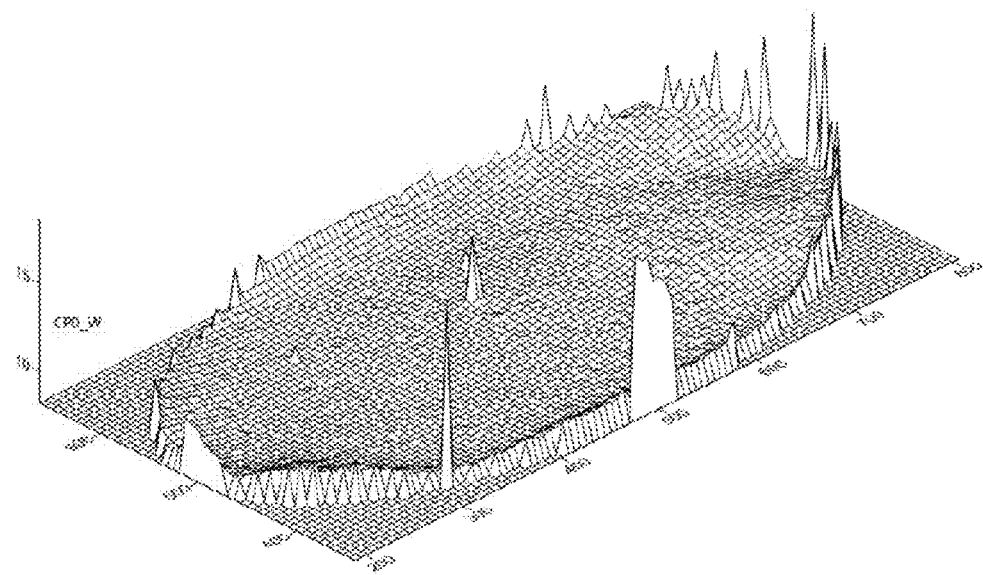

FIGS. 6A to 6G illustrate exemplary embodiments of spatial distributions of various parameters, including dominant wavelengths and various color parameters of a light emitting device. FIG. 6A illustrates that a SPD of the light emitting device is illustrated in a spatial distribution of dominant wavelengths of emitted photons. FIGS. 6B to 6G illustrate that the SPD of the light emitting device is de-convolved into a plurality sets of color parameters. In the illustrated embodiments, the SPD is de-convolved into two sets of color parameters. FIGS. 6B to 6D illustrate a first set of the color parameters (CP0) that is provided by a first Gaussian function. FIG. 6B is a spatial distribution of intensity of the emitted photons. FIG. 6C is a spatial distribution of center wavelength of the emitted photons. FIG. 6D is a spatial distribution of a curve width of the emitted photons. The CP0 set of color parameters may be used to illustrate, for example, a uniformity distribution of the light emitting device.

Figure 6E:
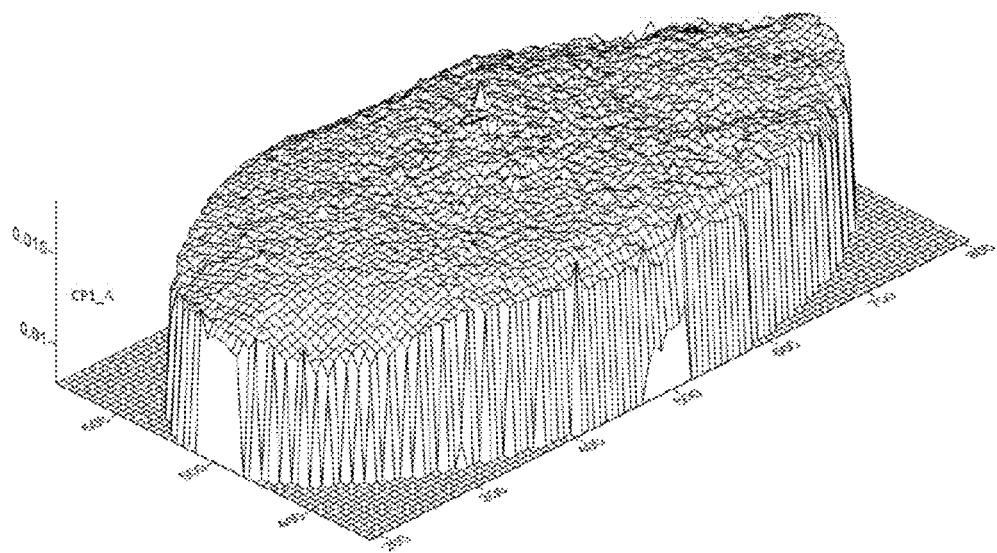
Figure 6F:
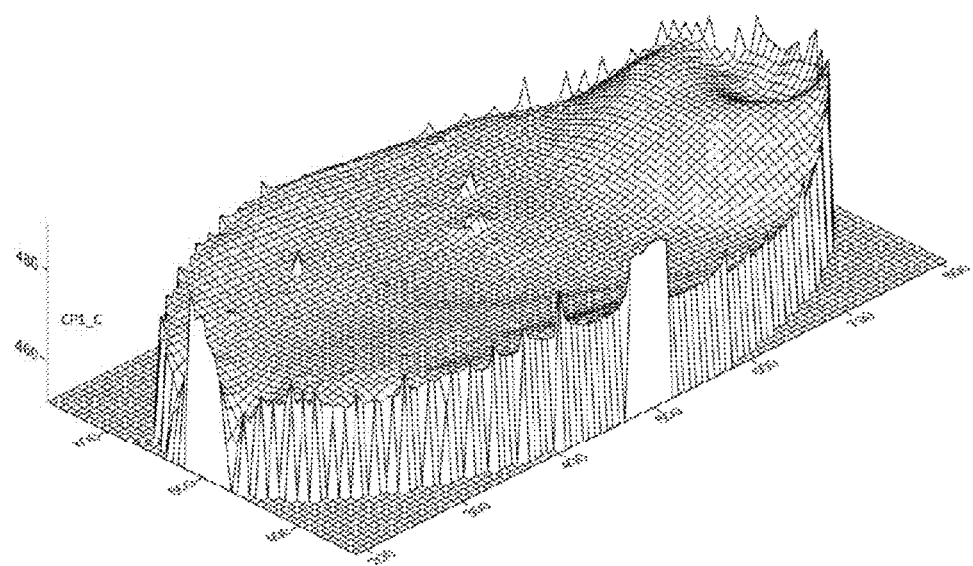
Figure 6G:
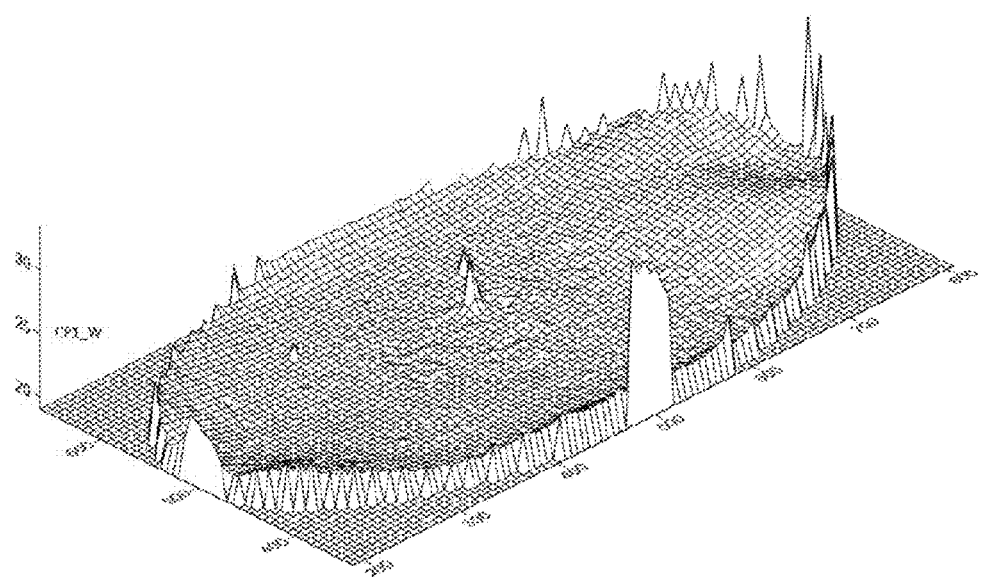

FIGS. 6E to 6G illustrate a second set of color parameters (CP1) that is provided by a second Gaussian function. FIG. 6E is a spatial distribution of intensity of the emitted photons. FIG. 6F is a spatial distribution of center wavelength of the emitted photons. FIG. 6G is a spatial distribution of a curve width of the emitted photons. The CP1 set of color parameters may be used to illustrate, for example, a thickness distribution of the light emitting device.

These and the other features of the present invention will become apparent to those skilled in the art from the above description. As it will be realized, the invention is capable of being modifiable in various obvious aspects, all without departing from the spirit and scope of the present invention. Also, it is appreciated that a system and method of quantifying color and intensity of a light emitting device may be implemented in various ways without departing from the scope of the present invention.

What is claimed is:

1. A method of characterizing a solid state light emitting device, comprising:
    exciting a first light emitting region of the solid state light emitting device;
    exciting a second light emitting region of the solid state light emitting device;
    collecting photons emitted by the first and second light emitting regions;
    obtaining a first spectral power distribution of the photons emitted by the first light emitting region;
    obtaining a second spectral power distribution of the photons emitted by the second light emitting region;
    obtaining, using a processor, at least one color parameter for the first spectral power distribution and at least one color parameter for the second spectral power distribution by fitting one or more Gaussian functions to the first and second spectral power distributions; and
    spatially correlating a physical property of the first and second light emitting regions based on the at least one color parameter for the first spectral power distribution and the at least one color parameter for the second spectral power distribution.

2. The method of claim 1, wherein the at least one color parameter for the first spectral power distribution and the at least one color parameter for the second spectral power distribution includes one or more of an intensity, a curve width, and a center wavelength of a Gaussian function of the one or more Gaussian functions.

3. The method of claim 1, wherein the first and second light emitting regions are a crystalline structure of the solid state light emitting device.

4. The method of claim 1, wherein the first and second light emitting regions are a region of a film deposited on a substrate of the solid state light emitting device.

5. The method of claim 1, wherein the physical property of the first and second light emitting regions of the solid state light emitting device includes one or more of thickness, uniformity, polarization, and/or defect density distribution of crystalline structures grown on or thin films deposited on a substrate during a manufacturing process of the solid state light emitting device.

6. The method of claim 1, further comprising:
    displaying a spatial distribution of the at least one color parameter for the first spectral power distribution and the at least one color parameter for the second spectral power distribution in one or more figures.

7. The method of claim 6, wherein the spatial distribution includes a spatial distribution of an intensity of the one or more Gaussian functions.

8. The method of claim 6, wherein the spatial distribution includes a spatial distribution of a center wavelength of a Gaussian function of the one or more Gaussian functions.

9. The method of claim 6, wherein the spatial distribution includes one or more wafer maps.

10. The method of claim 1, wherein exciting a first light emitting region and collecting photons emitted by the first light emitting region and exciting the second light emitting region and collecting photons emitted by the second light emitting region are obtained by moving the solid state light emitting device from the first light emitting region to the second light emitting region.

11. The method of claim 1, wherein the at least one color parameter for the first spectral power distribution and the at least one color parameter for the second spectral power distribution are configured to be optimized such that a difference between the first spectral power distribution and a summation of the one or more Gaussian functions or a difference between the second spectral power distribution and a summation of the one or more Gaussian functions is minimized according to an estimation process.

12. The method of claim 1, wherein the first light emitting region and the second light emitting region are spatially distinct from each other.

13. The method of claim 1, further comprising exciting the first light emitting region with a different device condition and obtaining a third spectral power distribution and obtaining at least one color parameter for the third spectral power distribution by fitting one or more Gaussian functions to the third spectral power distribution.

14. The method of claim 13, wherein the different device conditions include a different intensity of one of:
a device temperature, stimulating electric current intensity, time duration of a stimulating electric current, or a device age of the solid state light emitting device.

15. The method of claim 1, wherein obtaining at least one color parameter includes characterizing the first spectral power distribution using the fitting of the one or more Gaussian functions to the first spectral power distribution.

16. The method of claim 1, wherein the solid state light emitting device comprises a wafer substrate with solid state light emitting materials deposited on a surface of the wafer.

17. The method of claim 1, further comprising:
exciting a third light emitting region on a second solid state light emitting device; and
collecting photons emitted by the third light emitting region;
obtaining a third spectral power distribution of the photons emitted by the third light emitting region; and
obtaining, using the processor, at least one color parameter by fitting one or more Gaussian functions to the third spectral power distribution.

18. The method of claim 1, wherein the solid state light emitting device includes a blue light-emitting diode (LED) with a phosphor layer, wherein the at least one color parameter for the first spectral power distribution is obtained by fitting at least two Gaussian functions to the first spectral power distribution, and a contribution of the blue LED to the first spectral power distribution and a contribution of the phosphor layer to the first spectral power distribution is obtained by a de-convolution process of the at least one color parameter.

19. An apparatus for characterizing a solid state light emitting device, comprising:
a power source configured to be coupled to and excite a first and a second light emitting region on the solid state light emitting device;
a sensor that senses photons emitted by the first and second light emitting regions;
a spectrometer that obtains a first spectral power distribution of the photons emitted by the first light emitting region and a second spectral power distribution of the photons emitted by the second light emitting region; and
a processor that:
obtains at least one color parameter for the first spectral power distribution and at least one parameter for the second spectral power distribution by fitting one or more Gaussian functions to the first and second spectral power distributions, and
spatially correlates a physical property of the first and second light emitting regions based on the at least one color parameter for the first spectral power distribution and the at least one color parameter for the second spectral power distribution.

20. The apparatus of claim 19, wherein the at least one color parameter for the first spectral power distribution and the at least one color parameter for the second spectral power distribution includes one or more of an intensity, a curve width, and a center wavelength of a Gaussian function of the one or more Gaussian functions.

21. The apparatus of claim 19, wherein the first and second light emitting regions are a crystalline structure of the solid state light emitting device.

22. The apparatus of claim 19, wherein the first and second light emitting regions are a region of a film deposited on a substrate of the solid state light emitting device.

23. The apparatus of claim 19, wherein the physical property of the first and second light emitting regions of the solid state light emitting device includes one or more of thickness, uniformity, polarization, and/or defect density distribution of crystalline structures grown on or thin films deposited on a substrate during a manufacturing process of the solid state light emitting device.

24. The apparatus of claim 19, further comprising a movable platform, wherein the movable platform, the solid state light emitting device being movable with the movable platform, wherein the movable platform is configured such that the solid state light emitting device is movable between the first light emitting region and the second light emitting region.

25. The apparatus of claim 19, wherein the at least one color parameter for the first spectral power distribution and the at least one color parameter for the second spectral power distribution are configured to be optimized such that a difference between the first spectral power distribution and a summation of the one or more Gaussian functions or a difference between the second spectral power distribution and a summation of the one or more Gaussian functions is minimized according to an estimation process.

26. The apparatus of claim 19, wherein the first light emitting region and the second light emitting region are spatially distinct from each other.

27. The apparatus of claim 19, wherein the processor characterizes the first spectral power distribution using the fitting of the one or more Gaussian functions to the first spectral power distribution.

28. The apparatus of claim 19, wherein the solid state light emitting device comprises a wafer substrate with solid state light emitting materials deposited on a surface of the wafer.

29. The apparatus of claim 19, further comprising a third light emitting region on a second solid state light emitting device; wherein the sensor senses photons emitted by the third light emitting region, the spectrometer obtains a third spectral power distribution of the photons emitted by the third light emitting region; and the processor obtains at least one color parameter for the third spectral power distribution by fitting one or more Gaussian functions to the third spectral power distribution.

30. The apparatus of claim 19, wherein the solid state light emitting device includes a blue light-emitting diode (LED) with a phosphor layer, wherein the at least one color parameter for the first spectral power distribution is obtained by fitting at least two Gaussian functions to the first spectral power distribution, and a contribution of the blue LED to the first spectral power distribution and a contribution of the phosphor layer to the first spectral power distribution is obtained by a de-convolution process of the at least one color parameter.

31. The apparatus of claim 19, further comprising a display, wherein the processor causes a spatial distribution of the at least one color parameter for the first spectral power distribution and the at least one color parameter for the second spectral power distribution to be displayed on the display in one or more figures.

32. The apparatus of claim 31, wherein the spatial distribution includes a spatial distribution of an intensity of the one or more Gaussian functions.

33. The apparatus of claim 31, wherein the spatial distribution includes a spatial distribution of a center wavelength of a Gaussian function of the one or more Gaussian functions.

34. The apparatus of claim 31, wherein the spatial distribution includes one or more wafer maps.

* * * * *